United States Patent
Zivitz (10) Patent No.: US 6,858,433 B1
(45) Date of Patent: Feb. 22, 2005

(54) BIOSENSOR ELECTROMAGNETIC NOISE CANCELLATION

(75) Inventor: Maury Zivitz, Indianapolis, IN (US)

(73) Assignee: Roche Diagnostics Operations, Inc., Wilmington, DE (US)

(*) Notice: Subject to any disclaimer, the term of this patent is extended or adjusted under 35 U.S.C. 154(b) by 0 days.

(21) Appl. No.: 09/541,552

(22) Filed: Apr. 3, 2000

(51) Int. Cl.[7] .................. G01N 27/27; G01N 27/416; G01N 27/327; G01N 27/06

(52) U.S. Cl. ................ 436/151; 204/406; 205/775; 205/792; 422/82.01; 422/82.02; 422/98; 436/149; 436/150

(58) Field of Search .................. 204/406, 412, 204/416; 73/31.05, 31.06; 422/98, 82, 1, 82.02; 205/775, 777.5, 792; 436/66, 71, 95, 149–151

(56) References Cited

U.S. PATENT DOCUMENTS

| | | | |
|---|---|---|---|
| 3,961,248 A | * | 6/1976 | Kawamura |
| 4,164,539 A | * | 8/1979 | Johnston ...................... 422/96 |
| 4,225,410 A | * | 9/1980 | Pace ......................... 422/98 X |
| 4,233,033 A | * | 11/1980 | Eifler et al. ................ 422/98 X |
| 4,244,918 A | * | 1/1981 | Yasuda et al. ................. 422/95 |
| 4,277,439 A | * | 7/1981 | Yasuda et al. ................. 422/94 |
| 4,303,613 A | * | 12/1981 | Yasuda et al. ................. 422/95 |
| 4,387,359 A | * | 6/1983 | Tien et al. ................. 422/98 X |
| 4,426,621 A | | 1/1984 | Galway et al. |
| 4,571,543 A | * | 2/1986 | Raymond et al. ......... 422/98 X |
| 4,572,900 A | * | 2/1986 | Wohltjen .................... 436/151 |
| 4,589,970 A | * | 5/1986 | Ligtenberg et al. .......... 204/406 |
| 4,684,445 A | | 8/1987 | Seshimoto et al. ......... 204/1 T |
| 4,871,441 A | | 10/1989 | Tsunekawa et al. ......... 204/409 |
| 4,935,207 A | * | 6/1990 | Stanbro et al. ............ 422/68.1 |
| 4,999,582 A | | 3/1991 | Parks et al. .................. 324/438 |
| 5,017,340 A | * | 5/1991 | Pribat et al. .................... 422/98 |
| 5,030,418 A | | 7/1991 | Miyata ......................... 422/63 |
| 5,128,015 A | | 7/1992 | Szuminsky et al. ......... 204/403 |
| 5,141,868 A | * | 8/1992 | Shanks et al. ....... 422/82.02 X |
| 5,288,636 A | | 2/1994 | Pollmann et al. ........... 435/288 |
| 5,352,351 A | * | 10/1994 | White et al. ........... 304/403.04 |
| 5,672,256 A | * | 9/1997 | Yee ............................ 204/403 |
| 5,980,708 A | * | 11/1999 | Champagne et al. ....... 204/406 |
| 6,340,428 B1 | * | 1/2002 | Ikeda et al. ............... 205/777.5 |

FOREIGN PATENT DOCUMENTS

| | | | |
|---|---|---|---|
| JP | 65-119989 | * | 9/1979 |
| JP | 5-188037 | * | 7/1993 |
| JP | 5-203608 | * | 8/1993 |
| JP | 9-201337 | * | 8/1997 |
| WO | 89/02593 | * | 3/1989 |
| WO | 93/09433 | * | 5/1993 |

OTHER PUBLICATIONS

Shults, W. D. et al. Analytical Chemistry 1965, 37, 1415–16.*

Clark, L. C., Jr. Chemical Abstracts 1974, 80, abstract 45334e.*

Miaw, L.–H. L. et al, Analytical Chemistry 1979, 51, 1645–50.*

Hempstead, M.R. et al, Journal of Electroanalytical Chemistry 1984, 162, 1–□12.*

(List continued on next page.)

Primary Examiner—Arlen Soderquist
(74) Attorney, Agent, or Firm—Barnes & Thornburg (57) ABSTRACT

A biosensing cell assembly having a measurement loop with a test cell having an analyte reaction zone for amperometric measurement of a response current to determine analyte concentration and a noise cancellation loop arranged to be physically exposed to the same electromagnetic environment as the measurement loop. The noise cancellation loop has a predetermined impedance within a range of the impedance of the test cell analyte reaction zone and provides a current to cancel or reduce the effects of the electromagnetic environment on the measurement loop.

39 Claims, 6 Drawing Sheets

OTHER PUBLICATIONS

Richtering, W. et al, Electrochimica Acta 1989, 34, 1685–8.*
Kolev, S. D. et al., Analytica Chimica Acta 1993, 273, 71–80.*
Sarsfield, B. A. et al, Journal of Pharmaceutical Sciences 1998, 87, 1130–1137.*
Weber, S. G. et al, Industrial & Engineering Chemistry Product Research and Development 1981, 20, 593–598.*
Van Rooijen, H. W. et al, Journal of Liquid Chromatography 1983, 6, 2231–2254.*
Long, J. T. et al, Analytical Chemistry 1988, 60, 2309–2311.*
M. Collomb et al, Trav. Chim. Aliment. Hyg. 1991, 82, 174–186.*
O.I. Mateev J. Anal. Chem. 1989, 44, 298–299.*
E. S. Boltz et al, Rev. Prog. Quant. Nondestruct. Eval. 1998, 17A, 1043–1049.*
W. K. Ward et al, ASAIO J. 2000, 46, 540–546.*
Patent Abstract of JP vol. 018, No. 018 (P–1673), Dec. 1, 1994/& JP 05 256812 A, (Toto Ltd.) Aug. 10, 1993.
Patent Abstract of JP vo. 2000, no 07, Sep. 29, 2000/& JP 2000 124695 (Canon Inc.) A Apr. 28, 2000.

* cited by examiner

*Fig. 1*

PRIOR ART

BIOSENSOR ELECTROMAGNETIC NOISE CANCELLATION

BACKGROUND OF THE INVENTION

In the past, it has been found desirable to use amperometric analysis of biosensing cell assemblies. Such analysis was possibly subject to electromagnetic interference because of the loop formed by such cells in their disposable form, wherein a pair of conductors were supported on an insulating substrate with a remote test cell completing the circuit for analysis of a response current, which in one embodiment may be a Cottrell current. In the prior art, any stray electromagnetic fields present to the biosensing cell assembly may cause a spurious signal ("noise"), interfering with and distorting the response current. The present invention overcomes this difficulty by providing a noise cancellation apparatus and method to improve the measurement of the response current in such biosensing cell assemblies.

DETAILED DESCRIPTION OF THE INVENTION

Figure 1:
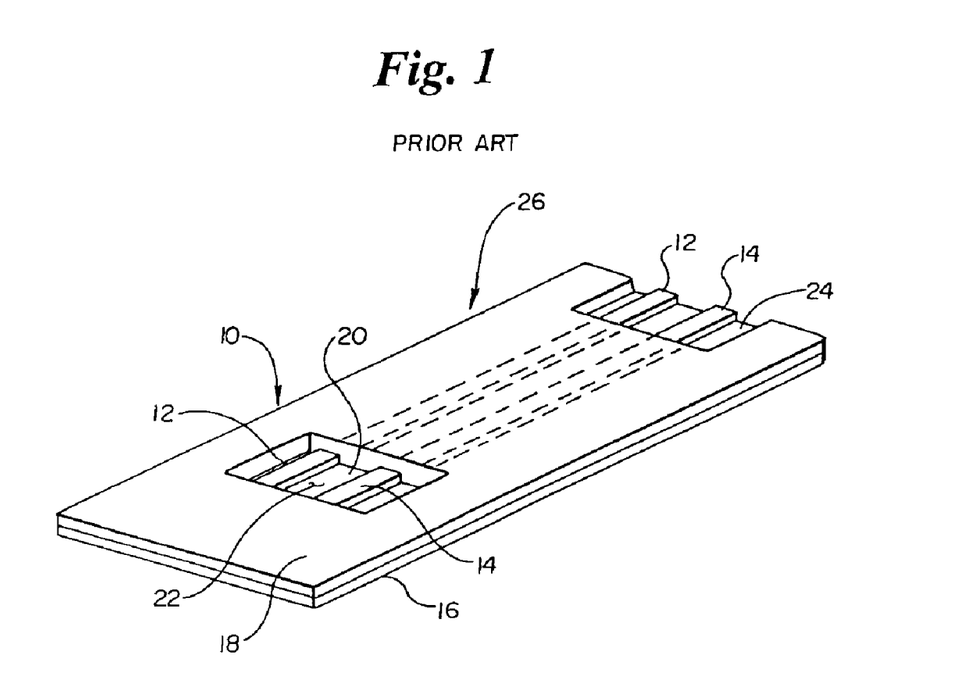
FIG. 1 is a prior art biosensing cell assembly.

Referring now to the figures, and most particularly to FIG. 1, a prior art biosensor cell assembly 10 includes a pair of electrodes or conductors 12 and 14 which are supported on a polymeric sheet or substrate 16. A cover sheet 18 is provided with openings 20 and 24 which expose the conductors 12 and 14. Opening 20 creates a well and provides access to a reaction zone 22 between conductors 12 and 14. A gel-like layer (not shown) or other form of reactants overlays conductors 12 and 14 to form reaction zone 22. In operation, an analyte-containing fluid sample is preferably placed on the reaction zone 22 to determine the concentration of analyte using amperometric analysis. The prior art assembly 10 may be subject to electromagnetic interference when undergoing amperometric analysis, more particularly, stray electromagnetic fields may pass through a measurement loop 26 formed by the conductors 12 and 14 and the reaction zone 22. It is to be understood that the measurement loop 26 will form a complete circuit when connected to an instrument (as will be described infra) to perform the amperometric analysis.

Figure 2:
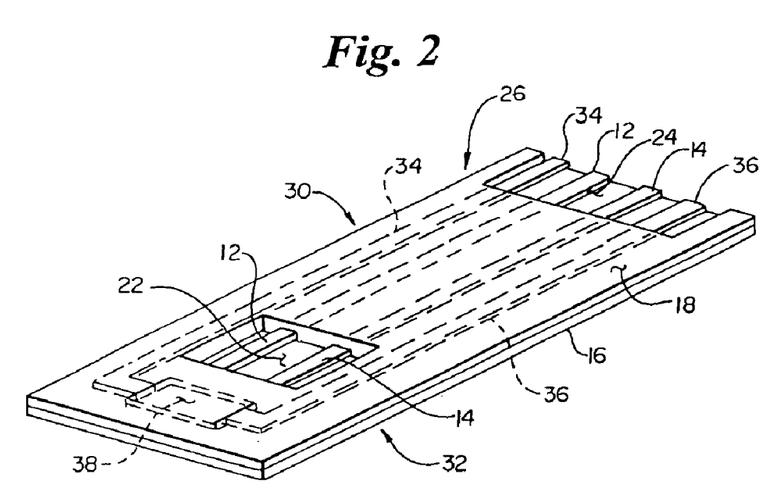
FIG. 2 is a biosensing cell assembly according to the present invention.

Referring now to FIG. 2, a first embodiment of the biosensor cell assembly 30 of the present invention may be seen. In this embodiment, the measurement loop 26 is the same or similar to that shown in FIG. 1. In addition, however, there is a noise cancellation loop 32 physically arranged to be exposed to substantially the same electromagnetic environment as the measurement loop 26. The noise cancellation loop 32 includes a pair of spaced apart conductors 34, 36 and a predetermined impedance 38. Impedance 38 may be a resistor and is preferably within a range of the impedance of the reaction zone or test cell 22 when the test cell 22 is amperometrically monitoring a response current to provide an indication of the analyte concentration being measured. For example, if the test cell 22 varies between 20K ohms and 100K ohms for various analyte concentrations to be measured, impedance 38 is preferably selected to be between 20K ohms and 100K ohms, and most preferably about 60K ohms, for a range of amperometric response currents from 10 to 50 microamperes.

As may be seen in FIG. 2, loop 32 closely surrounds loop 26, generally circumscribes the same area, and is in generally the same plane, so that any ambient electromagnetic field will affect or influence loops 26 and 32 substantially the same. More particularly, any error current induced in measurement loop 26 will be substantially the same as an error current induced in the noise cancellation loop 32. Since loop 32 has a known, fixed impedance, the error current may be removed from loop 26 by subtracting the error current in loop 32. It is to be understood that the error currents and error subtraction occur only when the assembly 30 is connected to an instrument for amperometric analysis.

Figure 3:
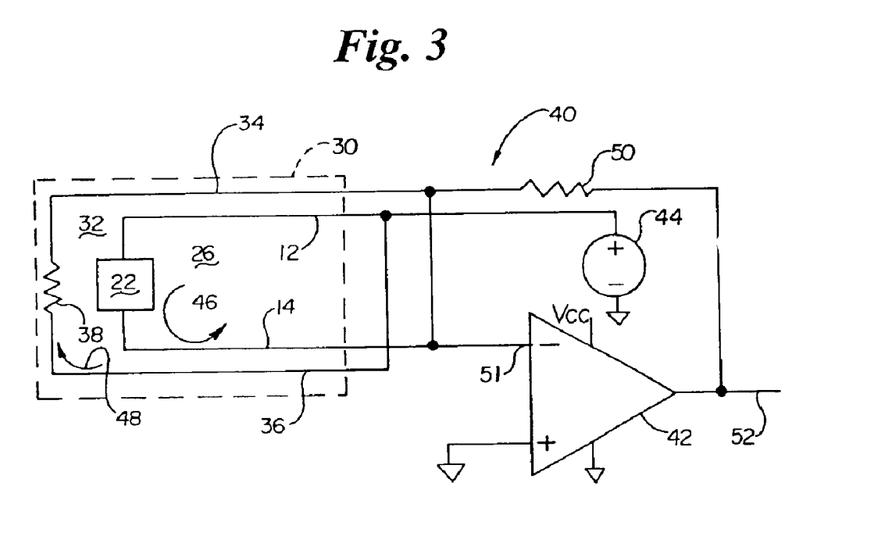
FIG. 3 is a circuit diagram of a simplified circuit useful for energizing and measuring the response current in the biosensing cell assembly of FIG. 2.

The electrical circuit schematic 40 for such a connection is shown in FIG. 3. In this circuit 40, test cell 22 is connected to an amplifier 42 and powered by a DC voltage source 44. Measurement loop 26 will thus have a response current flowing through conductors 12 and 14 in a counterclockwise direction 46. The noise cancellation loop 32, formed by conductors 34 and 36 and resistor 38 will have a current produced by source 44 flowing therethrough in a clockwise direction 48. Loop 32 may thus be seen to be arranged to be in an "anti-parallel" relationship with loop 26. Since a stray ambient electromagnetic field will induce substantially the same currents in each of loops 32 and 26 (i.e., the induced currents will be substantially the same in magnitude and in direction), the total currents in those loops may be added together at the negative summing junction 51 of amplifier 42, canceling or reducing the effect of the electromagnetic interference. It is to be understood that the DC current through resistor 38 will be a fixed offset to the response current in loop 26 and can be accounted for in a conventional manner. Resistor 38 preferably has a "flat" frequency response, such that the impedance in the noise cancellation loop 32 is substantially frequency independent. It is to be understood, however, that there is an inductance associated with each of the loops 26 and 32, and that such inductances are preferably made as similar as possible, such that the total impedance of loop 32 has substantially the same frequency response as the total impedance of loop 26, taking into account the conductors, any stray capacitance, and the test cell 22 (for loop 26) or resistor 38 (for loop 32). The voltage source 44 and amplifier 42 provide the means for determining the response current to provide an indication of an analyte concentration in the test cell or reaction zone 22.

It is to be further understood that the amperometric response current measured by the circuit 40 of FIG. 3 will have a modified characteristic from that when the prior art sensor 10 is used without the noise cancellation loop. More particularly, when the noise cancellation loop 32 is connected, the change in impedance of test cell 22 will be that of a variable resistor (depending upon analyte concentration) in parallel with a fixed resistor 38. The gain of circuit 40 will be the ratio of a feedback resistor 50 to the parallel equivalent of the impedances 22 and 38. Conventional offset and calibration subcircuits (not shown) may be used with amplifier 42 according to well-known techniques. It is to be understood that the output 52 of operational amplifier 42 is preferably further processed to provide signal conditioning by additional circuitry (also not shown). Such additional circuitry may include scaling, switching, and analog to digital conversion, as is well known for amperometric analysis of response currrents, for example measurement and display of glucose concentration in the reaction zone 22 by measurement of Cottrell current.

Figure 4:
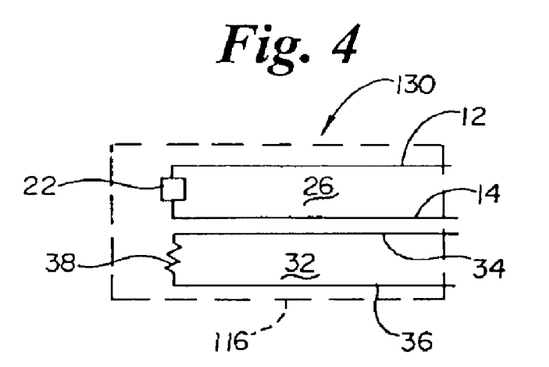
FIG. 4 is a simplified block diagram of the biosensing cell assembly of FIG. 2 and the circuit of FIG. 3.

Referring now to FIG. 4, an alternative embodiment of the biosensing cell assembly 130 may be seen. In this embodiment, the measurement loop 26 and the noise cancellation loop 32 are positioned adjacent each other on a common substrate 116. Even though the same field lines will not pass through both loops, such an arrangement will expose both loops to substantially the same electromagnetic environment, especially where field gradients are low, as is expected in the regions where amperometric analyses are expected to take place.

Figure 5:
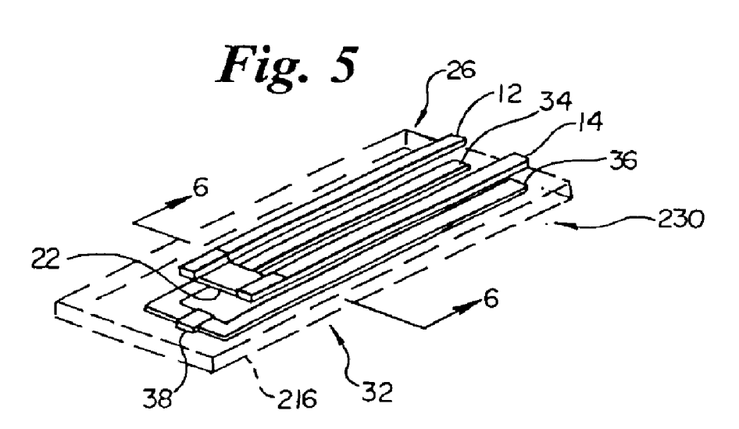
FIG. 5 is a second embodiment of a biosensing cell assembly according to the present invention.
Figure 6:
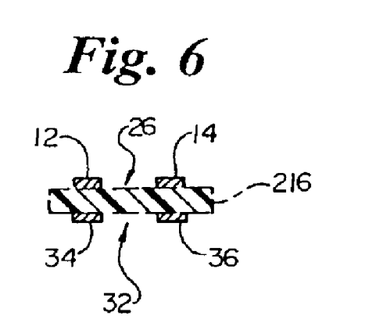
FIG. 6 is a section view along line 66 of FIG. 5.

Referring now to FIGS. 5 and 6, a still further alternative embodiment of a biosensing cell assembly 230 may be seen. In this embodiment, the measurement loop 26 is located on one side of a substrate 216, while the noise measurement loop 32 is located on other side of substrate 216. In this embodiment, loops 26 and 32 are preferably substantially congruent to each other and separated only by the thickness of substrate 216.

Figure 7:
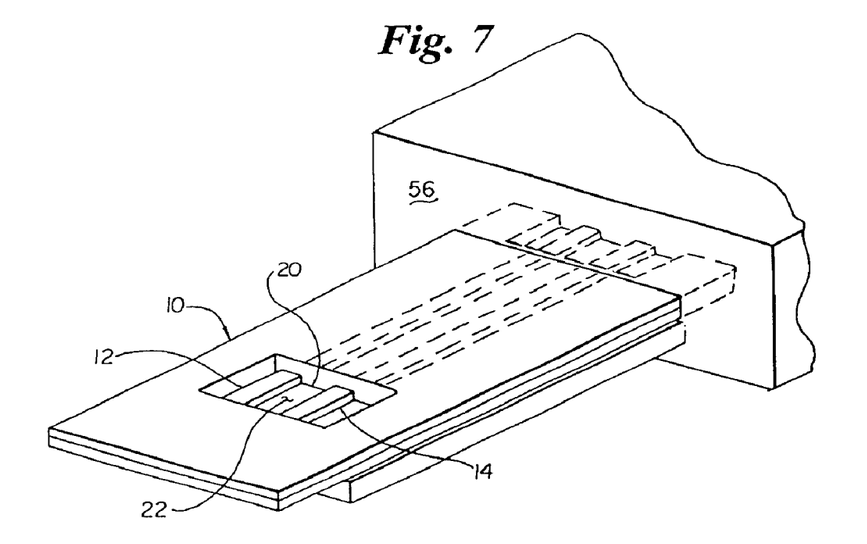
FIG. 7 is a still further embodiment of a biosensing cell assembly shown inserted into an instrument housing for energizing and reading the cell assembly according to the present invention.
Figure 8:
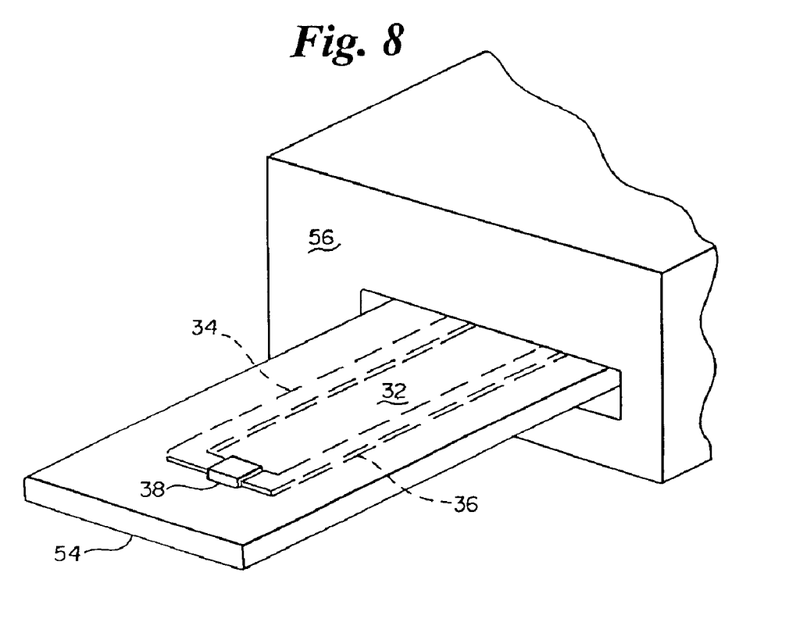
FIG. 8 is a view similar to that of FIG. 7, but with the biosensing cell assembly removed from the instrument housing and showing further aspects of this embodiment of the present invention.

Referring now to FIGS. 7 and 8, a still further alternative embodiment of the present invention may be seen. This embodiment makes use of the prior art biosensing cell assembly 10 and provides a shelf or support 54 carrying the noise cancellation loop 32. In operation, assembly 10 carrying conductors 12 and 14 and reaction zone 22 of the measurement loop 26 is inserted into a measuring instrument 56, as shown in FIG. 7. As may be most clearly seen in comparison with FIG. 8 (showing the noise cancellation loop 32 in shelf 54) the measurement loop 26 will be physically aligned with (and generally preferably substantially congruent to) the noise cancellation loop 32 when the test strip or assembly 10 is inserted into the instrument 56. Thus this embodiment has the instrument 56 electrically connectable to the measuring loop 26 and has the noise cancellation loop 32 located on the structure 54 adjacent the measurement loop 26 when the measurement loop is connected to the instrument.

Figure 9:
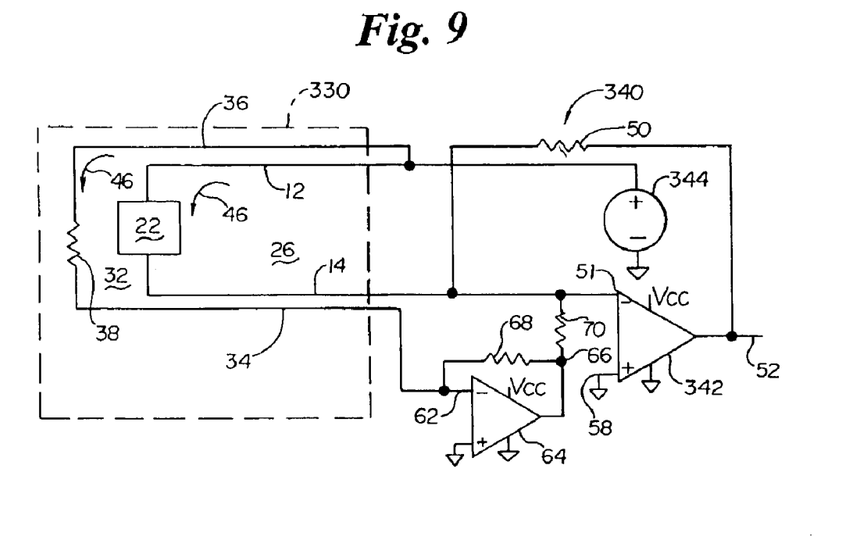
FIG. 9 is a simplified electrical schematic of another form of a circuit useful for energizing and measuring the response current in the biosensing cell assembly according to the present invention.

Referring now to FIG. 9, and alternative (simplified) schematic 340 for the biosensing cell assembly 330, power source 344 and amplifier 342 may be seen. In this embodiment it is to be understood that the response current caused by voltage source 344 flows in a counterclockwise direction 46 in the measurement loop 26. Similarly, current caused by voltage source 344 in the noise cancellation loop 32 flows in a counterclockwise direction, indicated by arrow 46. The noise cancellation loop 32 is connected to an inverting input 62 of an amplifier 64. An output 66 of amplifier 64 is connected through a summing resistor 70 to the inverting input 51 of amplifier 342. A feedback resistor 68 is connected between the inverting input 62 and the output 66 of amplifier 64. Feedback resistor 68 is preferably sized to set the gain of amplifier 64 in a conventional manner using the ration of the resistance of resistor 68 to the resistance of resistor 38 (assuming the impedance of source 344 is negligible). Summing resistor 70 is preferably selected to make the steady state output of the noise cancellation loop 32 equal to that of measurement loop 26.

In the embodiment shown in FIG. 9, it is to be understood that any stray electromagnetic field will cut both loops 26 and 32 substantially identically, and thus induce in-phase currents in each loop. By summing the output of the measurement loop 26 with an inverted signal (from amplifier 64) representing the output of the noise cancellation loop 32 at the inverting input 51 of amplifier 342, the error induced by a stray field in the electromagnetic environment may be effectively subtracted from the measurement loop signal. The resistance value of resistors 70 and 68 may be selected to optimize the error correction. By way of contrast, the phases of the electromagnetically induced signals or currents in the arrangement shown in FIGS. 2 and 3 are 180 degrees out of phase and thus need to be added to cancel.

Additionally, it is to be understood that when the effective impedances of loops 26 and 32 are unequal, the induced error currents will not cancel completely; however, in such circumstances, a reduction in error caused by induced currents from the electromagnetically propagated field energy irradiating the biosensor cell assembly will occur, even if the error is not eliminated entirely.

The present invention may thus be seen to include a method of reducing electromagnetic interference in a measurement loop of the type providing an indication of analyte concentration using a response current passing through a test cell by way of a pair of conductors on a substrate. In one form, the method includes physically aligning a noise cancellation loop with the measurement loop formed by the test cell and pair of conductors on a substrate, and connecting the noise cancellation loop in anti-parallel with the measurement loop such that any stray electromagnetic field induced current in the measurement loop is cancelled by a current induced by the same stray electromagnetic field in the noise cancellation loop. The method may include forming the noise cancellation loop and the measurement loop on the same test strip. Alternatively, the method may include providing the measurement loop on a disposable test strip and providing the noise cancellation loop on an instrument such that the noise cancellation loop is physically aligned with the measurement loop when the test strip is connected to the instrument.

This invention is not to be taken as limited to all of the details thereof as modifications and variations thereof may be made without departing from the spirit or scope of the invention.

What is claimed is:

1. A Cottrell current-type biosensing cell assembly comprising:
   a. a substrate having a proximal end and a distal end;
   b. a measurement loop located on the substrate, the measurement loop including:
      i. a pair of spaced-apart conductors each having a proximal end and a distal end, the proximal ends located at the proximal end of the substrate for connection to an instrument,
      ii. a test cell connected across the distal ends of the conductors, the test cell having an analyte reaction zone with an electrical impedance that varies in response to analyte concentration, the variation in electrical impedance of the analyte reaction zone in response to the application of an analyte, the concentration of which is to be determined, producing a Cottrell current-like profile; and c. a noise cancellation loop electrically distinct from the analyte reaction zone and physically arranged to be exposed to substantially the same electromagnetic environment as the measurement loop and electrically connected to substantially cancel the effect of electromagnetically propagated field energy irradiating the biosensor cell assembly.

2. The biosensing cell assembly of claim 1 wherein the noise cancellation loop is on the substrate.

3. The biosensing cell assembly of claim 2 wherein the measurement loop and the noise cancellation loop are on the same side of the substrate.

4. The biosensing cell assembly of claim 3 wherein the measurement loop and the noise cancellation loop circumscribe generally the same area.

5. The biosensing cell assembly of claim 3 wherein the measurement loop and the noise cancellation loop are located adjacent each other.

6. The biosensing cell assembly of claim 2 wherein the measurement loop and the noise cancellation loop are on opposite sides of the substrate.

7. The biosensing cell assembly of claim 6 wherein the measurement loop and the noise cancellation loop are substantially congruent.

8. The biosensing cell assembly of claim 1, further comprising an instrument electrically connectable to the measurement loop, and farther wherein the noise cancellation loop is located on a structure adjacent the measurement loop when the measurement loop is connected to the instrument.

9. The biosensing cell assembly of claim 8 wherein the noise cancellation loop is substantially congruent to the measurement loop.

10. The biosensing cell assembly of claim 1 wherein the measurement loop is physically arranged to have a first current induced therein having a first phase associated therewith when exposed to an ambient electromagnetic field and wherein the noise cancellation loop is physically arranged to have a second current induced therein, the second current having a second phase associated therewith when the noise cancellation loop is exposed to the same ambient electromagnetic field and wherein the first and second currents are combined to substantially reduce the effect of the ambient electromagnetic field on the biosensing cell assembly.

11. The biosensing cell of claim 10 wherein the first and second currents are combined to substantially cancel the effect of the ambient electromagnetic field on the biosensing cell assembly.

12. The biosensing cell assembly of claim 10 further including means for determining a response current to provide an indication of an analyte concentration.

13. The biosensing cell assembly of claim 12 wherein the means for determining the response current comprises a voltage source to apply a voltage across the test cell via the pair of conductors in the measurement loop and an amplifier connected to amplify the response current resulting therefrom.

14. The biosensing cell assembly of claim 13 wherein the measurement loop and the noise cancellation loop are physically arranged to have the phase of the second current displaced by 180 degrees from the phase of the first current and the measurement loop and the noise cancellation loop are electrically connected to add the first and second currents together.

15. The biosensing cell assembly of claim 13 wherein the measurement loop and the noise cancellation loop are physically arranged to have the first and second currents in phase with each other and the measurement loop and the noise cancellation loop are electrically connected to subtract the second current from the first current.

16. The biosensing cell assembly of claim 1 wherein the electrical impedance of the test cell varies within a predetermined range in response to various concentrations of the analyte.

17. The biosensing cell assembly of claim 16 wherein a predetermined impedance is included in the noise cancellation loop.

18. The biosensing cell assembly of claim 7 wherein the predetermined impedance included in the noise cancellation loop is within the impedance range of the test cell when the test cell is amperometrically monitoring a response current to provide an indication of the analyte concentration.

19. The biosensing cell assembly of claim 17 wherein the impedance in the noise cancellation loop is substantially frequency independent.

20. The biosensing cell assembly of claim 17 wherein the noise cancellation loop has a pair of conductors, and the combination of the impedance in the noise cancellation loop, together with the conductors of the noise cancellation loop, has substantially the same frequency response characteristics as the combination of the test cell and conductors of the measurement loop.

21. A method for adjusting the output of a Cottrell current-type biosensing cell assembly comprising:
a. a substrate having a proximal end and a distal end;
b. a measurement loop located on the substrate, the measurement loop including:
 i. a pair of spaced-apart conductors each having a proximal end and a distal end, the proximal ends located at the proximal end of the substrate for connection to an instrument,
 ii. a test cell connected across the distal ends of the conductors, the test cell having an analyte reaction zone with an electrical impedance that varies in response to analyte concentration, the variation in electrical impedance of the analyte reaction zone in response to the application of an analyte, the concentration of which is to be determined, producing a Cottrell current-like profile; the method including
c. providing a noise cancellation loop electrically distinct from the analyte reaction zone and physically arranged to be exposed to substantially the same electromagnetic environment as the measurement loop and electrically connected to substantially cancel the effect of electromagnetically propagated field energy irradiating the biosensor cell assembly.

22. The method of claim 21 wherein providing a noise cancellation loop comprises providing a noise cancellation loop on the substrate.

23. The method of claim 22 wherein providing the noise cancellation loop comprises providing a noise cancellation loop on the same side of the substrate as the measurement loop.

24. The method of claim 23 wherein providing the noise cancellation loop comprises providing a noise cancellation loop that circumscribes generally the same area as the measurement loop.

25. The method of claim 23 wherein providing the noise cancellation loop comprises providing a noise cancellation loop adjacent the measurement loop.

26. The method of claim 22 wherein providing the noise cancellation loop comprises providing a noise cancellation loop on an opposite side of the substrate from the measurement loop.

27. The method of claim 26 wherein providing the noise cancellation loop comprises providing a noise cancellation loop which is substantially congruent with the measurement loop.

28. The method of claim 21, further comprising providing an instrument electrically connectable to the measurement loop, and providing the noise cancellation loop comprises providing a noise cancellation loop on a structure adjacent the measurement loop when the measurement loop is connected to the instrument.

29. The method of claim 28 wherein providing the noise cancellation loop comprises providing a noise cancellation loop which is substantially congruent to the measurement loop.

30. The method of claim 21 wherein the measurement loop is physically arranged to have a first current induced therein having a first phase associated therewith when exposed to an ambient electromagnetic field and wherein providing the noise cancellation loop comprises providing a noise cancellation loop which is physically arranged to have a second current induced therein, the second current having a second phase associated therewith when the noise cancellation loop is exposed to the same ambient electromagnetic field and combining the first and second currents to substantially reduce the effect of the ambient electromagnetic field on the biosensing cell assembly.

31. The method of claim 30 wherein combining the first and second currents to substantially reduce the effect of the ambient electromagnetic filed on the biosensing cell assembly comprises combining the first and second currents to substantially cancel the effect of the ambient electromagnetic field on the biosensing cell assembly.

32. The method of claim 30 further including determining a response current to provide an indication of an analyte concentration.

33. The method of claim 32 wherein determining the response current comprises providing a voltage source to apply a voltage across the test cell via the pair of conductors in the measurement loop and providing an amplifier connected to amplify the response current resulting therefrom.

34. The method of claim 33 comprising arranging the measurement loop and the noise cancellation loop physically so that the phase of the second current is displaced by 180 degrees from the phase of the first current and electrically connecting the measurement loop and the noise cancellation loop to add the first and second currents together.

35. The method of claim 33 comprising physically arranging the measurement loop and the noise cancellation loop so that the first and second currents are in phase with each other and electrically connecting the measurement loop and the noise cancellation loop to subtract the second current from the first current.

36. The method of claim 21 wherein the electrical impedance of the test cell varies within a predetermined range in response to various concentrations of the analyte, providing a noise cancellation loop including providing in the noise cancellation loop a predetermined impedance.

37. The method of claim 36 wherein providing in, the noise cancellation loop a predetermined impedance comprises providing in the noise cancellation loop a predetermined impedance within the predetermined range of the electrical impedance of the test cell.

38. The method of claim 36 wherein providing in the noise cancellation loop a predetermined impedance comprises providing in the noise cancellation loop a predetermined impedance which is substantially frequency independent.

39. The method of claim 36 wherein providing a noise cancellation loop comprises providing a noise cancellation loop having a pair of conductors, the combination of the predetermined impedance and the pair of conductors of the noise cancellation loop having a frequency response characteristics which is substantially the same as the frequency response characteristic of the combination of the test cell and conductors of the measurement loop.

* * * * *